United States Patent [19]
Morita

[11] Patent Number: 5,271,900
[45] Date of Patent: Dec. 21, 1993

[54] CARBON ANALYZER FOR BOTH AQUEOUS SOLUTIONS AND SOLID SAMPLES

[75] Inventor: Youzo Morita, Kyoto, Japan

[73] Assignee: Shimadzu Corporation, Kyoto, Japan

[21] Appl. No.: 20,145

[22] Filed: Feb. 19, 1993

[51] Int. Cl.[5] ............... G01N 31/12; G01N 21/35
[52] U.S. Cl. ................................ 422/80; 422/82.05; 422/82.09; 436/145; 436/146; 250/356.1
[58] Field of Search ............ 422/78, 80, 82.05, 82.09; 436/145, 146, 155, 159, 160; 250/356; 73/23.31

[56] References Cited

U.S. PATENT DOCUMENTS

| | | |
|---|---|---|
| 3,296,435 | 1/1967 | Teal et al. ............................ 422/78 |
| 3,854,877 | 12/1974 | Csaky et al. ........................ 436/160 |
| 3,985,505 | 12/1976 | Bredeweg ........................... 436/145 |
| 4,271,124 | 6/1981 | Speeter ............................. 422/82.09 |
| 4,332,770 | 6/1982 | Ishida et al. ........................ 422/80 |

Primary Examiner—James C. Housel
Assistant Examiner—Jan M. Ludlow
Attorney, Agent, or Firm—Heller, Ehrman, White & McAuliffe

[57] ABSTRACT

A carbon analyzer capable of measuring carbon contents of both liquid and solid samples under appropriate conditions includes not only basic components of a total organic carbon (TOC) analyzer such as a carrier gas supplying unit 22, a sample injection unit 2 for a liquid sample 6, a liquid sample combustion-oxidation vessel 12 and a $CO_2$ detector 46, but also a solid sample intake unit 26 for receiving a solid sample, converting its carbon components into $CO_2$ and sending it into the $CO_2$ detector 46 together with a carrier gas. The $CO_2$ detector 46 is a non-dispersive infrared analyzer with two measuring cells 48a and 48b having different lengths and disposed in series with a light flux such that the light flux will have different optical path lengths through these measuring cells 48a and 48b. A switching valve 44 serves to direct the gas to be tested selectively to either of the measuring cells 48a and 48b and the carrier gas to the other as a purge gas.

8 Claims, 2 Drawing Sheets

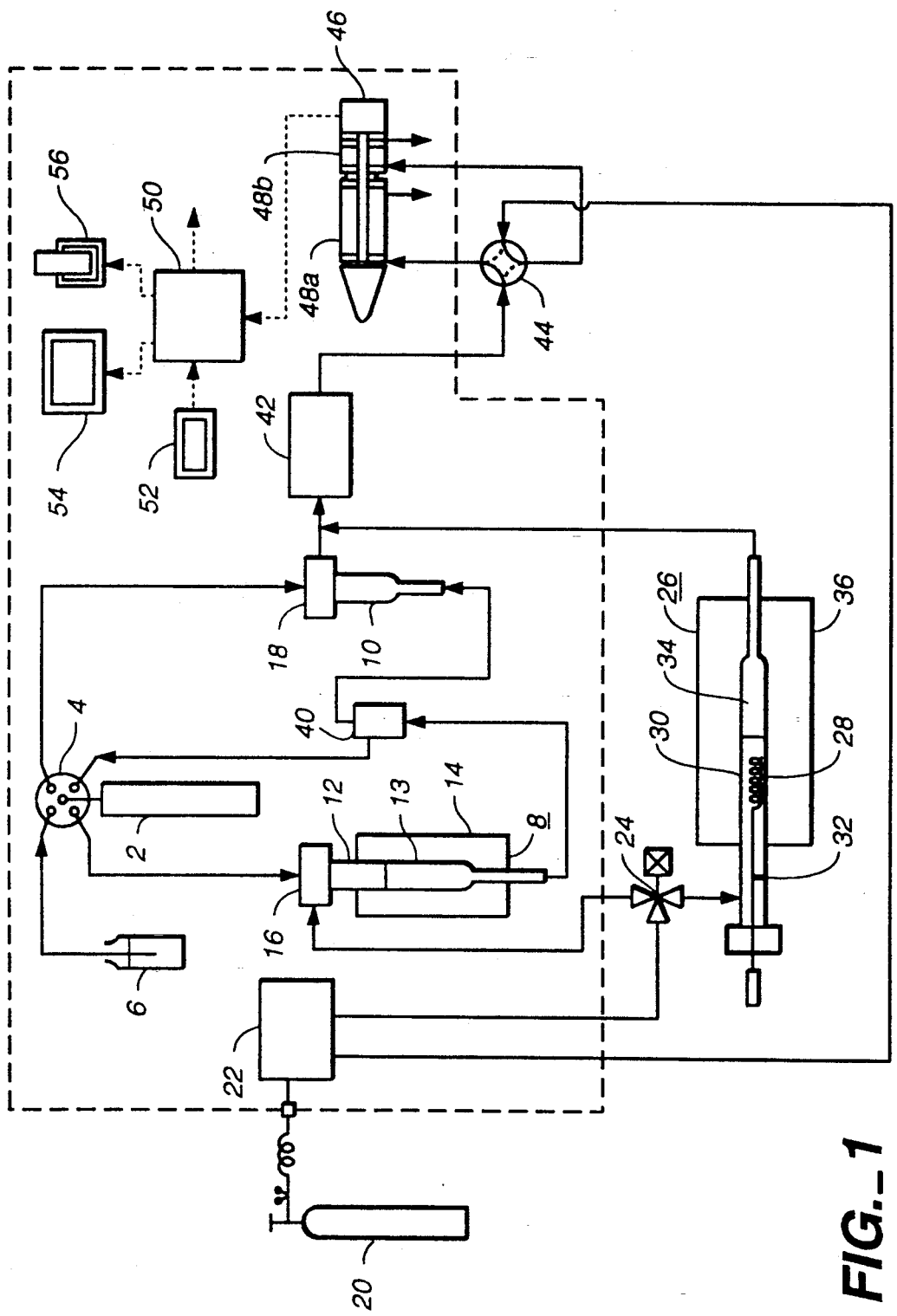
FIG._1

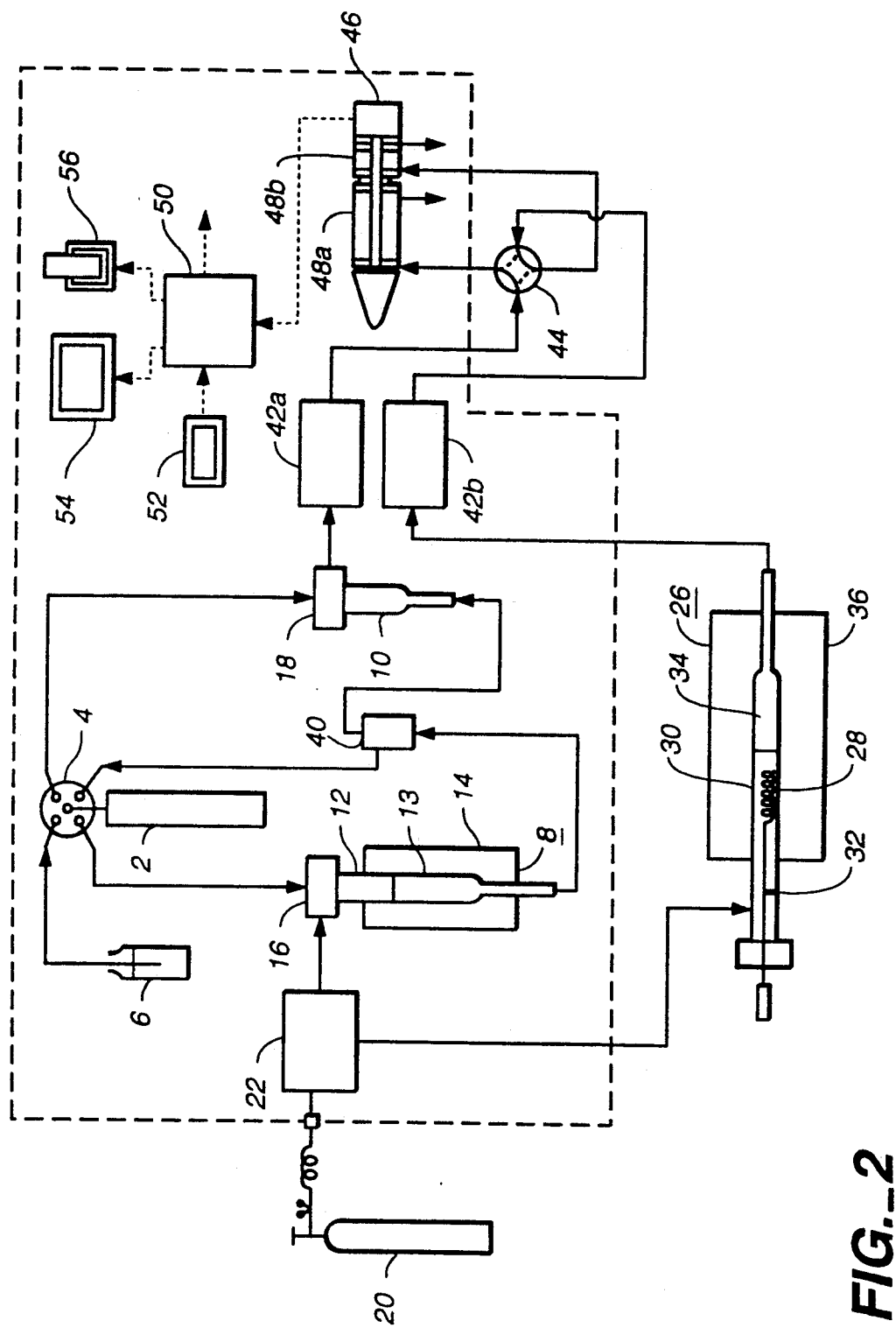
FIG._2

CARBON ANALYZER FOR BOTH AQUEOUS SOLUTIONS AND SOLID SAMPLES

BACKGROUND OF THE INVENTION

This invention relates to a carbon analyzer, and more particularly to an apparatus for measuring both the total organic carbon (TOC) content of a sample in the form of aqueous solution and the carbon content of a solid sample.

For the purpose of providing a carbon detector for both samples in the form of an aqueous solution (hereinafter referred to as liquid samples) and solid samples, it has been known to modify a TOC analyzer with a carrier gas supplying unit, a sample injection unit, a combustion-oxidation reaction unit and a $CO_2$ detector for measuring the total organic carbon content of an aqueous solution by adding thereto a solid sample supplying unit adapted to convert the carbon component of a solid sample into $CO_2$ in a solid sample combustion-oxidation unit and to transport it to the aforementioned $CO_2$ detector together with a carrier gas. Use is made, for example, of a non-dispersive infrared (NDIR) gas analyzer as the $CO_2$ detector. In other words, the measuring cell of this NDIR analyzer is used in common for the measurement of gases in both flow routes for liquid and solid samples.

In the case of a liquid sample, TOC measurements in the range of several ppm to several 100 ppm are of principal importance, and several 10 $\mu$l (or several 10 mg) of the sample is usually used. It is difficult, however, to inject a large amount of such a sample into a combustion-oxidation reaction tube at high temperature because its water component is suddenly vaporized and increases its volume. On the other hand, the carbon content of solid samples is much higher, ranging between several 1000 ppm to several %. The weight of a solid sample can be easily measured by a balance, and it is preferable to make use of several 10—several 100 mg of a sample in order to prevent uneven carbon concentration. This means that about 100 times more $CO_2$ is generated from a solid sample than from a liquid sample.

Since most carbon analyzers are designed primarily for samples in the form of aqueous solution, the NDIR measuring cells are also designed primarily for samples in the form of aqueous solution. If such a measuring cell is used for the measurement of a solid sample, either the measurement can be done only for a lower concentration of carbon or only a small amount of the sample can be used.

It is therefore an object of the present invention to provide a carbon analyzer capable of measuring the carbon content of both aqueous solutions and solid samples under appropriate conditions.

It is another object of the invention to provide a carbon analyzer capable of varying sensitivity of measurements when there is a change in the carbon concentration in the sample or the amount of the sample changes.

SUMMARY OF THE INVENTION

A carbon analyzer embodying the invention, with which the above and other objects can be accomplished, may be characterized as being basically a TOC analyzer having a carrier gas supplying unit, a liquid sample injection unit, a combustion-oxidation reaction unit and a $CO_2$ detector for measuring the total organic carbon content of a liquid sample, and also comprising a solid sample supplying unit adapted to convert the carbon component of a solid sample into $CO_2$ in a solid sample combustion-oxidation unit and to transport it to the aforementioned $CO_2$ detector together with a carrier gas. As the $CO_2$ detector, use is made of a non-dispersive infrared gas analyzer having two measuring cells with different optical path lengths for the light flux for measurement, disposed in series with respect to the light flux. The gas from the flow route for a liquid sample is led to the measuring cell with longer optical path length and the gas from the flow route for a solid sample is led to the measuring cell with shorter optical path length.

For the purpose of varying the sensitivity of measurement, a switching means is provided between the flow routes for the liquid and solid samples and the $CO_2$ detector such that the sample-containing gas can be selectably directed to either of two measuring cells.

The sensitivity becomes higher with a measuring cell with a longer optical path length for the light flux for measurement. It becomes lower with a measuring cell with a shorter optical path length for the light flux for measurement. Since the amount of $CO_2$ gas generated from a liquid sample is small and that from a solid sample is large, the gas from a liquid sample is generally directed to the measuring cell with a longer optical path length and the gas from a solid sample is generally directed to the measuring cell with a shorter optical path length for measurement.

In the case of a solid sample with an extremely low carbon concentration, the switching means may be operated to increase the sensitivity of measurement by directing the gas from the solid sample to the measuring cell with a longer optical path length.

BRIEF DESCRIPTION OF THE DRAWINGS

The accompanying drawings, which are incorporated in and form a part of this specification, illustrate embodiments of the invention and, together with the description, serve to explain the principles of the invention. In the drawings:

FIG. 1 is a structural diagram of a carbon analyzer embodying the present invention; and FIG. 2 is a structural diagram of another carbon analyzer also embodying the present invention.

DETAILED DESCRIPTION OF THE INVENTION

As shown in FIG. 1, a carbon analyzer embodying the present invention is provided with a liquid sample injector 2 and a liquid sample switching valve 4. A specified amount of a liquid sample 6 is collected by the sample injector 2 and transported into a combustion-oxidation reaction unit 8 or an IC (inorganic carbon) reaction vessel 10 through the liquid sample switching valve 4. The combustion-oxidation reaction unit 8 is provided with a TC (total carbon) combustion tube 12 packed with an oxidation catalyst 13 and a heating furnace 14 for heating the combustion tube 12 from outside. A required amount of the sample 6 is injected into the combustion tube 12 through a TC injection port 16 of a slide type, and the unnecessary portion is discharged into a drain (not shown) by sliding the TC injection port 16. The IC reaction vessel 10 also functions similarly to inject a required amount of the sample 6 and to discharge the unnecessary portion into a drain (not shown) by the operation of a slide-like IC injection port 18. In order to supply a carrier gas, there is a cylinder 20 filled with a pure oxygen gas or high-purity air with $CO_2$ and hydrocarbons removed therefrom. The oxygen-containing gas from the cylinder 20 is supplied as a carrier gas through a gas flow control unit 22. The carrier gas is supplied selectively either to the combustion-oxidation reaction unit 8 or to a solid sample intake unit 26 by means of a carrier gas switching valve 24.

Inside the solid sample intake unit 26, a solid sample such as soil and mud is placed on a boat made of ceramic platinum or quartz and inserted into a solid sample combustion tube 30 by means of a push bar 32. The combustion tube 32 is packed with an oxidation catalyst 34 and is surrounded by a furnace 36 (for heating to a temperature of about 900° C.). The carbon component emitted from the solid sample on the boat 28 is sent into the oxidation catalyst 34 together with the carrier gas containing oxygen and is burnt and oxidized to become $CO_2$ gas.

The gas from the combustion-oxidation reaction unit 8 is passed through an ultra-pure water trap 40 for blank check and sent from the IC reaction vessel 10 to a dehumidifier/gas pretreatment unit 42. The gas from the combustion tube 30 of the solid sample intake unit 26 is also sent to the same dehumidifier/gas pretreatment unit 42. The gas which has been dehumidified in the dehumidifier/gas pretreatment unit 42 is directed to a NDIR gas analyzer 46 comprised of a longer cell 48a and a shorter cell 48b arranged in series with respect to the light flux for measurement. The longer cell 48a is used generally as a measuring cell for a liquid sample, having an optical path length of about 200 mm. The shorter cell 48b is used generally as a measuring cell for a solid sample, having an optical path length of about 1 mm. The gas from the dehumidifier/gas pretreatment unit 42 is directed by a measuring cell switching valve 44 either into the longer cell 48a or into the shorter cell 48b. In the meantime, the carrier gas is passed as a purge gas from the gas flow control unit 22 through the switching valve 44 into the other of the cells 48a and 48b, into which the gas to be tested is not being directed. The trap 40 is for producing ultra-pure water not containing carbon for the measurement of a blank and introducing it through the sample injector 2 into this analyzer 46.

Signals outputted from the NDIR analyzer 46 are transmitted to a data processing unit 50 to be processed. Numerals 52, 54 and 56 indicate a keyboard, a liquid crystal display and a printer, respectively. The data processing unit 50 may be made connectable to a computer through an RS-232C connector.

In FIG. 1, the area surrounded by broken lines represents an organic carbon detector for the measurement of a liquid sample. The carrier gas cylinder 20, the solid sample intake unit 26 and the measuring cell switching valve 44 may be regarded as externally connected components. This, however, is not intended to limit the scope of the invention. The solid sample intake unit 26 and the measuring cell switching valve 44 may be unistructurally formed with the organic carbon detector.

The operation of the carbon analyzer shown in FIG. 1 will be explained next.

If the measurement is for a liquid sample, the carrier gas switching valve 24 is switched away from the solid sample intake unit 26, and the measuring cell switching valve 44 is switched in the direction of the longer cell 48a (with a longer optical path). For the measurement of total carbon (TC), the liquid sample 6 is collected in the sample injector 2 and injected into the combustion tube 12. The total carbon in the sample 6 is oxidized into $CO_2$ by the oxidizing catalyst 13 inside the combustion tube 12 and is passed through the dehumidifier/gas pretreatment unit 42 together with the carrier gas into the longer cell 48a of the NDIR analyzer 46 where the total carbon (TC) is measured. In the meantime, the carrier gas is introduced into the shorter cell 48b to serve as a purge gas. For the measurement of inorganic carbon (IC), the liquid sample 6 is collected in the sample injector 2 and injected into the IC reaction vessel 10. Inorganic carbon is converted into $CO_2$ inside the IC reaction vessel 10, passed through the dehumidifier/gas pretreatment unit 42 together with the carrier gas into the longer cell 48a of the NDIR analyzer 46 where the inorganic carbon (IC) is measured. The total organic carbon (TOC) is calculated by the formula: $TOC = TC - IC$.

If the measurement is for a solid sample, the carrier gas switching valve 24 is switched in the direction of the solid sample combustion tube 30, and the measuring cell switching valve 44 is switched in the direction of the shorter cell 48b (with a shorter optical path). A measured amount of the solid sample is placed on the boat 28 and is heated such that the $CO_2$ gas generated inside the combustion tube 30 is passed through the dehumidifier/gas pretreatment unit 42 together with the carrier gas into the shorter cell 48b of the NDI analyzer 46 to be detected therein. In the meantime, the carrier gas is introduced into the longer cell 48a to serve as a purge gas.

In the case of a solid sample with a very small carbon content, the gas to be measured may be guided into the longer cell 48a in order to improve the sensitivity. Similarly, in the case of a liquid sample with TOC concentration on the order of %, use may be made of the shorter cell 48b in order to reduce the sensitivity. According to the present invention, a wider range of measurement can be obtained by selectively using either the longer or shorter cell. Another carbon analyzer embodying the present invention is shown in FIG. 2. This embodiment is characterized in that the carrier gas is passed through the gas flow control unit 22 and directed simultaneously to both of the combustion tubes 12 and 30. The gas from the flow path for a liquid sample and the gas from the flow path for a solid sample are separately directed into different dehumidifier/gas pretreatment units 42a and 42b. The gas from the flow path for a liquid sample is eventually directed into the longer cell 48a, and the gas from the flow path for a solid sample is eventually directed into the shorter cell 48b.

At the time of the measurement, either a liquid sample or a solid sample is introduced into this analyzer and the generated $CO_2$ gas is introduced into one of the cells 48a or 48b. Only the carrier gas is introduced through the measuring cell switching valve 44 into the other of the cells 48a and 48b to serve as a purge gas to prevent the atmospheric air from entering the system.

The embodiment shown in FIG. 2 is further characterized in that the measuring cell switching valve 44 is disposed between the pair of dehumidifier/gas pretreatment units 42a and 42b and the pair of (longer and shorter) cells 48a and 48b such that the gas from the flow route for either a liquid sample or a solid sample can be directed to either the longer cell 48a or the shorter cell 48b. Although the gas from a liquid sample is usually directed into the longer cell 48a and the gas from a solid sample is usually directed into the shorter cell 48b, the measuring cell switching valve 44 may be switched otherwise, depending on the carbon concentration of the sample being analyzed.

In summary, a NDIR analyzer is used as a $CO_2$ detector according to the present invention and two cells with different optical lengths are placed in series with respect to the light flux for measurement. As a result, both liquid samples and solid samples can be analyzed by a single carbon analyzer under optimum conditions (such as carbon concentration and the amount of sample). When the analyzer is used only for solid samples or only for liquid samples, measurements are possible under a wider range by using different ones of the cells, depending on the carbon concentration and the amount of the sample.

What is claimed is:

1. In a carbon analyzer comprising a total organic carbon analyzer for measuring the total organic carbon in a liquid sample, said analyzer including a $CO_2$ detector, a carrier gas supplying means, a liquid sample injection means for injecting a liquid sample into a carrier gas supplied from said carrier gas supplying means, a liquid sample combustion-oxidation vessel in communication with said carrier gas supplying means, including means for oxidizing said injected liquid sample to thereby generate a $CO_2$-containing gas, and a first gas flow route through which said $CO_2$-containing gas is directed to said $CO_2$ detector; the improvement wherein said carbon analyzer further comprises a solid sample processing means for converting carbon contents of a solid sample into $CO_2$, means for directing said $CO_2$ from said solid sample and said carrier gas together to said $CO_2$ detector through a second gas flow route; said $CO_2$ detector comprising a non-dispersive infrared gas analyzer providing a flux of infrared light and including a longer measuring cell and a shorter measuring cell disposed in series with respect to said flux, said longer measuring cell having a longer optical path length therethrough than said shorter measuring cell for said flux of light; said first gas flow route being connected to said longer measuring cell; and said second gas flow route being connected to said shorter measuring cell.

2. The carbon analyzer of claim 1 further comprising a carrier gas switching means for directing said carrier gas from said carrier gas supplying means selectively to said liquid sample combustion-oxidation vessel for to said solid sample processing means.

3. In a carbon analyzer comprising a total organic carbon analyzer for measuring the total organic carbon in a liquid sample, said analyzer include $CO_2$ detector, a carrier gas supplying means, a liquid sample injection means for injecting a liquid sample into a carrier gas supplied from said carrier gas supplying means, a liquid sample combustion-oxidation vessel in communication with said carrier gas supplying means, including means for oxidizing said injected liquid sample to thereby generate a $CO_2$-containing gas, and a first flow route through which said $CO_2$-containing gas is directed to said $CO_2$ detector; the improvement wherein said carbon analyzer further comprises a solid sample processing means converting carbon contents of a solid sample into $CO_2$, means for directing said $CO_2$ from said solid sample and said carrier gas together to said $CO_2$ detector through a second gas flow route; said $CO_2$ detector comprising a non-dispersive infrared gas analyzer providing a flux of infrared light and including a longer measuring cell and a shorter measuring cell disposed in series with respect to said flux, said longer measuring cell having a longer optical path length therethrough than said shorter measuring cell for said flux of light; and said carbon detector further comprising a measuring cell switching means for connecting selectably either said first or second gas flow route to selectively either said longer or shorter measuring cell.

4. The carbon analyzer of claim 3 further comprising a carrier gas switching means for directing said carrier gas from said carrier gas supplying means selectively to said liquid sample combustion-oxidation vessel or to said solid sample processing means.

5. The carbon analyzer of claim 3 wherein said measuring cell switching means automatically connects said first gas flow route to said longer measuring cell if said second gas flow route is connected to said shorter measuring cell, and automatically connects said first gas flow route to said shorter measuring cell if said second gas flow route is connected to said longer measuring cell.

6. The carbon analyzer of claim 5 wherein said first and second gas flow routes each include a gas dehumidifying means in communication with said measuring cell switching means.

7. The carbon analyzer of claim 3 wherein said measuring cell switching means automatically connects said carrier gas supplying means to said longer measuring cell if either said first or second gas flow route is connected to said shorter measuring cell, and automatically connects said carrier gas supplying means to said shorter measuring cell if either said first or second gas flow route is connected to said longer measuring cell.

8. The carbon analyzer of claim 7 wherein said total organic carbon analyzer further includes a single gas dehumidifying means in communication with both said first and second gas flow routes and to said measuring cell switching means.

* * * * *